(12) United States Patent
Bicak et al.

(10) Patent No.: US 9,788,548 B2
(45) Date of Patent: Oct. 17, 2017

(54) SYNTHESIS OF PURE DIALLYL MORPHOLINIUM MONOMERS IN HIGH YIELDS AND USING ANTIBACTERIAL EFFECT OF THEIR SPIRO POLYMERS

(71) Applicant: Tugrul Cem Bicak, Istanbul (TR)

(72) Inventors: Tugrul Cem Bicak, Istanbul (TR); Ahmet Ince, Istanbul (TR); Niyazi Bicak, Istanbul (TR)

(73) Assignee: Tugrul Cem BICAK, Istanbul (TR)

( * ) Notice: Subject to any disclaimer, the term of this patent is extended or adjusted under 35 U.S.C. 154(b) by 0 days.

(21) Appl. No.: 15/103,883

(22) PCT Filed: Dec. 15, 2014

(86) PCT No.: PCT/TR2014/000507
§ 371 (c)(1),
(2) Date: Jun. 13, 2016

(87) PCT Pub. No.: WO2015/088464
PCT Pub. Date: Jun. 18, 2015

(65) Prior Publication Data
US 2016/0286809 A1 Oct. 6, 2016

(30) Foreign Application Priority Data
Dec. 13, 2013 (TR) .............................. a 2013 14672

(51) Int. Cl.
| | |
|---|---|
| *A01N 43/84* | (2006.01) |
| *A61K 31/787* | (2006.01) |
| *C08F 26/02* | (2006.01) |
| *C08F 226/02* | (2006.01) |

(52) U.S. Cl.
CPC ............ *A01N 43/84* (2013.01); *A61K 31/787* (2013.01); *C08F 26/02* (2013.01); *C08F 226/02* (2013.01)

(58) Field of Classification Search
CPC ........ C08F 226/02; C08F 26/02; A01N 43/84; A61K 31/787
See application file for complete search history.

(56) References Cited

U.S. PATENT DOCUMENTS

| | | |
|---|---|---|
| 4,443,363 A | 4/1984 | Klinger et al. |
| 5,348,678 A | 9/1994 | Hodam, Jr. et al. |
| 5,575,993 A | 11/1996 | Ward et al. |
| 5,965,514 A | 10/1999 | Wierenga et al. |
| 6,153,568 A | 11/2000 | McCanna et al. |
| 6,159,929 A | 12/2000 | Snowden et al. |
| 6,277,897 B1 | 8/2001 | Nohr et al. |
| 6,325,862 B1 | 12/2001 | Otsuki |
| 6,444,628 B2 | 9/2002 | Nocerino et al. |
| 6,596,681 B1 | 7/2003 | Mahieu et al. |
| 6,762,162 B1 | 7/2004 | Valpey, III et al. |

OTHER PUBLICATIONS

Butler G B et al"Preparation and polymerization of unsaturated quaternary ammonium compounds", Journal of the American Chemical Society, American Chemical Society, US, vol. 71, No. 9, Sep. 1, 1949, pp. 3120-3122.
Niyazi Bicak et al "Synthesis and polymerization of N, N-diallyl morpholinium bromide", European Polymer Journal, Pergamon Press Ltd. Oxford, GB, vol. 36, No. 4, Apr. 1, 2000, pp. 703-710.
Niyazi Bicak et al"Synthesis of N-allyl morpholine and its copolymers with sulfur dioxide and styrene"Designed Monomers and Polymers, 1998, vol. 1, p. 305-313.

*Primary Examiner* — Robert A Wax
*Assistant Examiner* — William Craigo
(74) *Attorney, Agent, or Firm* — Gokalp Bayramoglu

(57) ABSTRACT

Herein, the synthesis of N,Ndiallyl morpholinium monomers and polymerization of the same to form rings at high yield and purity are explained. The process involves the synthesis of N,Ndiallyl morpholinium bromide and chloride and subsequently partially or completely exchanging their anions with borate, p-toluenesulfonate, oleate, and acetate anions. The cyclopolimerization of monomers yields water soluble polymers carrying quaternary ammonium groups in each repeated unit, whose aqueous solutions act as a bactericide solution. These solutions are advantageous in preparation of antibacterial formulations intended for domestic use. The polymer with bromide and borate anions is an efficient antibacterial which is able to kill "*Pseudomonas Aeruginosa*", the hardest hospital bacterium to cope with, as well as various common bacteria. These formulations are suitable for producing bactericide wet wipes and forming abacterial surfaces and, when combined with air conditioners, generating bacteria free air.

10 Claims, No Drawings

SYNTHESIS OF PURE DIALLYL MORPHOLINIUM MONOMERS IN HIGH YIELDS AND USING ANTIBACTERIAL EFFECT OF THEIR SPIRO POLYMERS

FIELD OF THE INVENTION

This invention relates to synthesis of diallylammonium monomers with different counter ions and their Spiro polymers in high yields and discovery of their extraordinary bacteria killing effect.

DESCRIPTION OF THE PRIOR ART

Quaternary ammonium compounds are known to show antibacterial effects. These compounds have been employed as additives of various formulations for water-based disinfecting/cleaning solutions, sterilizing solutions for medical devices and dental protection components etc. Common approach for such formulations is the use of quaternary ammonium compounds (quats) as antibacterial or disinfecting material in combination with surface active agents. Other additives such as perfumes, colorants and antioxidants are secondary components. In such formulations quaternary ammonium compounds may be either monomeric or polymeric (polyquats). In order to impart a good hydrophyllyphophyl balance (HLB), long alkyl chains are introduced to monomeric quaternary amines. Incorporation of $C_{15}$-$C_{26}$ alkyl chains is common approach to induce surfactant effect in addition to the primary antibacterial functionality.

Thus, the U.S. Pat. No. 4,443,363 teaches the use of alkoxylated alcohols or phenols together with monomeric quaternary alkyl amines for preparing detergents with disinfecting effects. In addition, the patent (U.S. Pat. No. 5,348,678) describes dental cleaning solutions containing quaternary ammoniums.

The patents (U.S. Pat. Nos. 5,965,514 and 6,159,929) describe the use of amine oxides as cosurfactants with disinfectant quaternary amines for cleaning of waxed floors and for preparing disinfectant formulations respectively.

Availability of new developed quaternary amine polymers brought possible application of these materials as nonvolatile long-lasting antibacterial components in disinfecting/cleaning formulations. For instance, a cleaning wipe impregnated with a solution consisting of quaternary amine ureas or poly (hexamethylene biguanidine) hydrochloride has been described (U.S. Pat. No. 6,596,681).

In another patent (U.S. Pat. No. 6,762,162) a quaternary ammonium biocide, quaternized dimethylamino ethyl methacrylate homo or co-polymers have been demonstrated to use as bacteria killing component in combination with a nonionic surfactant. A cleaning spray formulation containing a polymer electrolyte, consisting of cationic poly (ethyleneimine) has been presented in U.S. Pat. No. 6,325,862 for efficient stain removal and disinfection.

Various quaternary amine polymers, such as quaternized chitosan, poly (dimethyl diallyl ammonium chloride) and homo-and co-polymers of 1-vinyl 3-methyl imidazolinium chloride have been used in hair shampoo formulations (U.S. Pat. No. 6,444,628) as antibacterial components. Ionenes constituting with quaternary nitrogen connecting units in the main chain have also been used (U.S. Pat. No. 5,575,993) as antibacterial component together with some bioactive anions. Polybiguanidines and polyimidazolinium have been used in contact lenses (U.S. Pat. No. 6,153,568) to prevent bacteria growth. U.S. Pat. No. 6,277,897 discloses the use of quaternized dimethylamino ethyl acrylate polymers together with dialkyl diallyl ammonium polymers in skin-care formulations.

Synthesis of N,N-Diallyl morholinium (DAM) monomers and their polymers have been reported in 1949 by Buttler and Bunch (G. B. Butler, R. L Bunch. 3 Am Chem Soc 1949;71,3120). Since NMR was not available at that time structure of its polymer was not clear.

In the following papers (N Bicak, A. B Soydan, S Cakaloglu. Des. Mon and Polym. 1998;1:305 and N. Bicak, B. F. Senkal Eur. Polym. J. 36 (2000) 703-710), synthesis of DAM-bromide by stepwise allyation of morholine and its cyclopoymerization has been described. However practical yield reported for the first step allylation product, N-ally morpholine is considerably low (55-72%). Our ongoing works indicate that, presence of water in the reaction medium is responsible for the low conversion in the first allylation step.

The monomer diallylmorpholinium bromide (DAM bromide) obtained by quaternization of N-ally morpholine has been reported to polymerize using t-butyl hydroperoxide in aqueous solutions. However, in that paper polymerization yields and molecular weights of the resulting products are considerably low. Especially, the polymerization yields depend on monomer concentration. Moreover diallyl morpholinium salts with different counter anions have not been reported so far in the literature.

SUMMARY OF THE INVENTION

The present invention is concerned with synthesis of diallyl morpholinium based polymers as new and very, efficient antibacterial polymers starting from allyl halides and morpholine. The tri-step process involves;

i) monoallylation of morpholine ii) quaternization of N-allyl morpholine, iii) anion exchange of diallylmorpmolinium salt and followed polymerization as depicted in Scheme 1.

Scheme 1. Three-step process for synthesis antibacterial dially morpholinium polymers starting from morpholine and allyl halides.

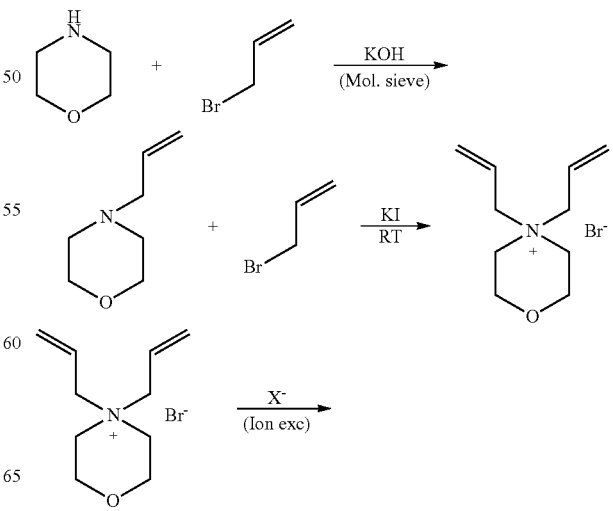

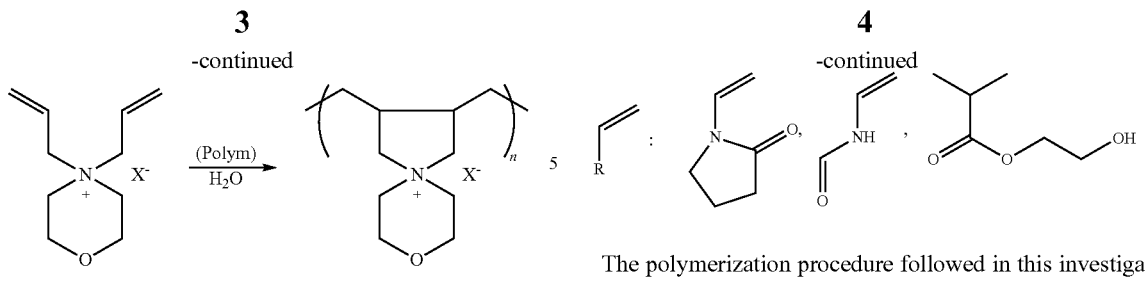

In contrast to low monoallylation yields of the reported procedures, the procedure disclosed in this invention provides high yields in the reaction with allyl bromide. This new procedure is simply based on continuous removal of water from the reaction medium using molecular sieves. The practical allylation yield for the case with allyl bromide is as high as 98%, which has not been attained before. Quaternization N-allyl morpholine with allyl bromide in the absence of solvent gives also high yields as reported in the literature. However this procedure results in very hard solid material within 5 h, mechanical disintegration of which is very difficult.

The procedure being disclosed in this invention is different, in which 0.1 g solid KI is added for half mole (63.5 g) of N-allyl morpholine together with 2 mL dry acetone. This modification reduces the quaternization time down to 2 days and the resulting white solid becomes easily breakable. Moreover, work up and isolation of N,N-diallymorholinium bromide in dry atmosphere in the present investigation provides highly pure product, as inferred from elemental microanalysis, $^1$-HNMR and C13-NMR spectra.

Diallymorpholinium bromide or chloride can be polymerized before or after changing the counter anions. Although polymerization of N,N-diallymorholinium bromide has been reported in the literature, the initiator t-butylhydroperoxide employed gives only low molecular weight polymers. Similar low molecular weight polymers have been reported by initiation with $K_2S_2O_8$ as reported for polymerization of another quaternary ammonium monomer, N,N-diallyl N,N-dimethylammonium chloride (DADMAC). The molecular weights estimated by viscosities measured in salt solutions do not exceed 6000-8000 Da.

Scheme 2. Copolymerization of N,N-diallyl morpholinium salts with some water miscible vinyl monomers.

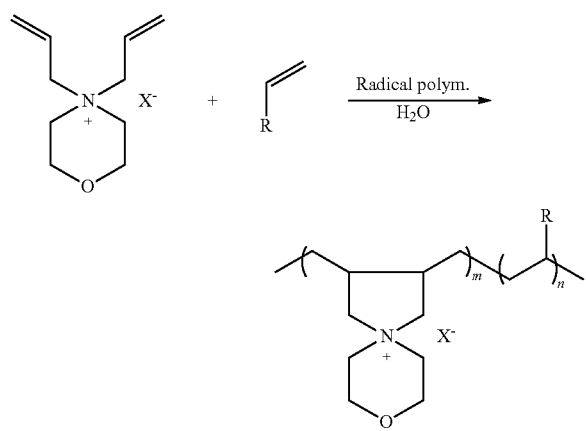

The polymerization procedure followed in this investigation eliminates those drawbacks and provides high molecular weights as high as 40.000 Da, when the polymerizations are carried out in concentrated aqueous solutions (50-62%), using a water soluble radical initiator, 2,2'-azobis(2-methyl propiondiamidine) dihydrochloride. The polymers precipitated in water (12-25% v/v)—acetone mixtures do not show residual double bonds in their $^1$HNMR spectra, implying purity of the resulting materials.

The procedure followed for the polymerization of N,N-diallymorholinium bromide can be employed for the monomer with different counter anions, except methanol-water mixture is preferred for the case of the monomer with oleate counter anion.

The aqueous polymerization medium described in this embodiment is also suitable to produce copolymers with N-vinyl pyrrolidinone (NVP), N-vinyl formamide (NVF) and 2-hydroxyethylmethacrylate (HEMA). The monomer with any counter anion described here can be used in copolymerization with these comonomers, as shown in Scheme 2.

The copolymerizations in principle can be carried out in any percent of comonomer composition. Molar ratio of the comonomers can be chosen in 0-80% range, depending on the area to be used. For instance, the copolymer with HEMA is can be considered to employ as a component of antibacterial composite with acrylate esters. In that case molar ratio of HEMA is chosen preferably in 60-80% range. The comonomer ratios estimated by $^1$HNMR spectra of resulting copolymers nearly match with the feed compositions of the copolymerizations.

DETAILED DESCRIPTION OF THE INVENTION

Object of this invention is to obtain water soluble N,N-diallyl morpholinium spiropolymers in high purities and high yields. It is another object of this invention to provide chemically inert poly (diallyl morpholinium) salts with long term stability. Chemical inertness described herein refers to stability against acidic, reducing and oxidizing agents. It is an object of this invention to provide synthetic procedure for preparing N,N-diallyl morpholinium bromide or chloride in high yields and high purities. The monomer is obtained by condensation of morpholine with allyl halides in two-step reaction, wherein, in the first stage 1 mole of allyl chloride or bromide is reacted with 1 mole of morpholine in methanol (at least 100 mL per mole of morpholine).

In this step an acid-trapping agent such as KOH or NaOH is essential to increase the condensation yield. However, this is not enough to increase allylation yield, because presence of water in the medium causes to considerably low yields. To remove water, from the methanol solution molecular sieves in 3 A° pore size are used. To remove 1 mole of water, 65 g molecular sieve is placed in a flask with two necks at the top and bottom. The flask is connected between the reaction flask and reflux condenser. Such system removes water continuously from the reaction medium. By refluxing 6 h for the case using allyl bromide subsequent filtration and distillation of the liquid residue at 147-151° C. gives high yields of N-allyl morpholine (95-98%). $^1$H-NMR spectrum (in CDCl3), δ: 2.40 ppm (t, 4H), 3.0 ppm (d, 2H, —CH$_2$—O), 3.7 ppm (t, 4H, CH$_2$—N), 5.15 (d, 2H, =CH$_2$), 5.80 (m, 1H, —CH=).

The molecular sieves used in the process can be recovered by heating at 400° C. for 2 h. In the second step, 1 mole of allyl bromide (or chloride) is gradually added to 1 mole of N-allyl morpholine obtained in the first step, while stirring. It is best to carry out this reaction without additional solvent in an Erlenmeyer flask made of polypropylene. In case for using allyl bromide an effective cooling of the mixture is essential to suppress the violent reaction at the beginning. This is achieved by drop wise addition of allybromide at 0° C.

After stirring of the mixture for 2 h, 0.05 g solid KI is added to the medium as catalyst. In this case, the whole reaction content solidifies within 6-8 h. However, it is best to conduct the reaction for 48 h to increase the yield. In the case of using allylchloride solidification takes within 15 days at room temperature. In each case, the solid is broken up and dispersed in a mixture of 50 mL dry acetone and 50 mL of diethyl ether by means of rotating scraper blade.

The product N, N-diallyl morpholinium halide is collected by suction and dried under vacuum at room temperature. The practical yield is 94-98% when the manipulations are made in dry atmosphere using a dry-box system. Elemental microanalysis, found (calculated for $C_{10}H_{18}NOBr$), C: 47.10% (48.38%), H: 7.40% (7.26%), N: 5.48% (5.64%). $^1$HNMR spectrum (in DMSO-d$_6$), δ: 6.1 ppm (m, 2 H, —CH= protons), 5.7 ppm(m, 4 H, =CH$_2$), 4.1 ppm(d, 4 H, allylic CH$_2$), 4.0 ppm(t, 4 H, N—CH$_2$—), 3.42 ppm (t, 4 H, O—CH$_2$—). C13-NMR spectrum (in DMSO-d$_6$), δ: 57.0 ppm (C—N—),60.0 ppm (C—O—), 60.5 ppm (allylic —CH$_2$—), 125 ppm (=CH$_2$—), 128 ppm (—CH=). Melting point: 211-212° C.

It is important to note that the reaction yield with allyl chloride is somewhat low (85-92%) in the same conditions.

Diallymorpholinium borate, p-toluenesulfonate or oleate can be obtained by anion exchange. Polymerization of these monomers in concentrated aqueous solutions gives high molecular weight polymers, using 2,2'-azobis (2-methyl propiondiamidine) dihydrochloride (AMPD) as radical initiator. The use of butylhydroperoxide or $K_2S_2O_8$ as initiator in polymerization of N,N-diallymorholinium bromide has been reported to give low molecular weight polymers. In the present procedure those drawbacks have been eliminated by polymerization in concentrated solutions, using AMPD initiator. The polymers isolated by precipitation in water (12-25% v/v)—acetone mixtures are highly pure, so that their $^1$HNMR spectra do not show monomer residues.

The general procedure and polymerization receipt used for the polymerization of N,N-diallymorholinium bromide can be employed for the monomers with different counter anions. This procedure can also be used to prepare copolymers of the quaternary ammonium monomers with suitable comonomers such as N-vinyl pyrrolidinone (NVP), N-vinyl formamide (NVF) and 2-hydroxyethylmethacrylate (HEMA) as shown in Scheme 2.

Molar ratio of the comonomer to the morpholinium monomer can be varied 0-80% range. The ratio is adjusted depending on the area to be used. For instance to use the copolymer as a component of antibacterial composite with acrylic esters, molar ratio HEMA is chosen preferably in 60-80% range. For reparing water based antibacterial formulations on the other hand, NVF or NVP is preferred as comonomer. One another aspect of the present invention is to provide a process for making water-soluble antibacterial polymer solutions and formulations using N,N-diallyl morpholinium homo and copolymers. The following examples are given to explain the procedures used in this invention.

EXAMPLE 1

Preparation of N-Allyl Morpholine:
Added to a suitable reactor equipped with a reflux condenser and a dropping funnel were 87 parts of redistilled morpholine and 100 parts of dry methanol. Meanwhile a two-way flask containing 65 parts of molecular sieve (3 A°) was connected between the reactor and reflux condenser. While stirring, 121 parts of allyl bromide was introduced by drop wise addition through a pressure-equalizing dropping funnel at 0° C. Addition takes place 45-60 minutes. Slow addition is essential to control exothermic reaction in the reactor. After addition has completed, the mixture was stirred for 2 h at room temperature. Then, nearly half of the methanol solution containing 40 parts of NaOH in 100 parts methanol was added drop wise to the reaction mixture within 30 min. The reaction content was slowly heated to 80° C. for 2 h. At this point another half portion of the remaining methanol solution of NaOH was introduced by slow addition and the mixture was slowly heated to 80° C. for another 2 h. Remaining portion of NaOH solution was added to the mixture and the reaction was conducted by refluxing for 3 h.

The mixture was cooled and filtered to remove NaBr from the reaction mixture. The filtrate and washings were combined with and nearly all the methanol was distilled off by means of a rotavapor. The liquid residue was then distilled and the fraction in 153-161° C. of boiling range was collected as colorless liquid. The yield of the product, N-allyl morpholine was 120-124 g in (94-98%) % range.

EXAMPLE 2

Preparation of N,N-Diallyl Morpholinium Bromide:
63.5 parts of N-allyl morpholine was charged to an Erlenmeyer flask made of polyethylene and equipped with a reflux condenser a dropping funnel. While stirring at room temperature, 63.3 parts of allyl bromide was added drop wise into the reactor in about 30 min. While stirring 0.1 part of solid KI was added to the mixture as catalyst together with 0.5 part acetone. The reaction content was left to stand at room temperature for 72 h. To the hard solid precipitated, there was added 120 parts of acetone-diethyl ether mixture containing 0.05 part hydroquinone as radical scavenger. Then the solid was broken by a blender having sharpened blades and filtered under dry atmosphere. Finally, it was washed with 30 parts of dry ether. The product is very hygroscopic and must be stored in a tightly closed container in dry atmosphere.

EXAMPLE 3

Preparation of N,N-Diallyl Morpholinium Chloride:
Similar experimental setup was used for the synthesis of N-diallyl morpholinium chloride. Thus, 63.5 parts of N-allyl morpholine is charged to a suitable reactor equipped with a reflux condenser a dropping funnel. While stirring at room temperature, 40 parts of allyl chloride is added drop wise into the reactor in about 30 min. Then 0.1 part of solid KI was added to the mixture as catalyst. The reaction content is left to stand at room temperature for 15 days. The hard solid precipitated was broken out by means of a blender and filtered under dry atmosphere. Finally, it was washed with 30 parts of dry ether. The product is very hygroscopic and must be stored in a tightly closed bottles.

EXAMPLE 4

Anion Exchange of N,N-Diallyl Morpholinium Chloride with Sodium Borate:

In a 250 mL of canonical flask 51 g N,N-diallyl morpholinium chloride was dissolved in 20 mL water. This solution was mixed with a solution of 17 g $NaBO_2$ in 50 mL 2-methoxyethanol. Then one-third of the solution was evaporated by rotavapor. The solution was heated to 100° C. and filtered: The filtrate was evaporated to dryness and the solid residue (48-51 g) was stored in a tightly closed bottle.

EXAMPLE 5

Anion Exchange of N,N-Diallyl Morpholinium Chloride with Potassium Oleate:

In a 250 mL of canonical flask 51 g N,N-diallyl morpholinium chloride was dissolved in 20 mL water. This solution was thoroughly mixed with 321 g (1.0 mol) potassium oleate. Then 300 mL of ethanol was added to the mixture and boiled for 15 min and filtered while hot. Ethanol was evaporated by rotavapor. The waxy residue was transferred to a tightly closed bottle.

EXAMPLE 6

Anion Exchange of N,N-Diallyl Morpholinium Chloride with Potassium P-Toluenesulfonate:

In a 250 mL of canonical flask 47 g para-toluenesulfonic acid monohydrate ($C_7H_8SO_3.H_2O$) (0.25 mol) was dissolved in 50 mL water. To this solution there was added a solution of 14 g KOH in 15 mL distilled water. The mixture was stirred for 20 min at room temperature and thoroughly mixed with aqueous solution of 51 g N,N-diallyl morpholinium chloride in 20 mL water.

Nearly half of the solution was evaporated by rotevaporator. Then 150 mL 2-methoxyethanol was added to this solution and heated to 110° C. for 30 min. The mixture was filtered while hot. The solvent was then completely evaporated by rotevaporator and the solid residue was stored in a tightly closed bottle.

EXAMPLE 7

Polymerization of N,N-Diallyl Morpholinium Chloride:

In a 500 mL of canonical flask equipped with a reflux condenser, pressure equalized dropping funnel and a nitrogen inlet, there was added 30 mL of distilled water and 0.68 g 2,2'-azobis(2-methyl propiondiamidine dihydrochloride ($2.5 \times 10^{-3}$ mole). While passing a nitrogen flow from the solution, 51 g N,N-diallyl morpholinium chloride (0.25 mole) was added and stirred until clear solution (approximately 30 min). The nitrogen flow was stopped and the system was closed. The reaction was conducted for 8 h under continuous stirring at 65° C. The reaction content was cooled to room temperature and poured into 120 mL acetone. The polymer precipitated was collected by suction, washed with acetone (25 mL) and dried at 80° C. for 24 h. The resulting hygroscopic polymer (49.2 g) was stored in tightly closed bottle.

EXAMPLE 8

Polymerization of N,N-Diallyl Morpholinium Bromide:

In a 500 mL of canonical flask equipped with a reflux condenser, pressure equalized dropping funnel and a nitrogen inlet, there was added 35 mL of distilled water and 0.68 g 2,2'-azobis(2-methyl propiondiamidine dihydrochloride ($2.5 \times 10^{-3}$ mol). While passing a nitrogen flow from the solution, 62 g N,N-diallyl morpholinium bromide (0.25 mol) was added and stirred until clear solution (approximately 30 min). The nitrogen flow was stopped and the system was closed. The reaction was conducted for 8 h under continuous stirring at 65° C. The reaction content was cooled to room temperature and poured into 150 mL acetone. The polymer precipitated was collected by suction, washed with acetone 25 mL and dried at 80° C. for 24 h. The resulting hygroscopic polymer (59.7 g) was stored in tightly closed bottle.

EXAMPLE 9

Polymerization of N,N-Diallyl Morpholinium Borate:

In a 500 mL of canonical flask equipped with a reflux condenser, pressure equalized dropping funnel and a nitrogen inlet, there was added 31 mL of distilled water and 0.68 g 2,2'-azobis(2-methyl propiondiamidine dihydrochloride ($2.5 \times 10^{-3}$ mol). While passing a nitrogen flow from the solution, 52.7 g N,N-diallyl morpholinium borate (0.25 mol) was added and stirred until clear solution (approximately 30 min) had obtained. The nitrogen flow was stopped and the system was closed. The reaction was conducted for 8 h under continuous stirring at 65° C. The reaction content was cooled to room temperature and poured into 150 mL acetone. The polymer precipitated was collected by suction, washed with acetone 25 mL and dried at 80° C. for 24 h. The resulting hygroscopic polymer (50.4 g) was stored in tightly closed bottle.

EXAMPLE 10

Polymerization of N,N-Diallyl Morpholinium P-Toluenesulfonate:

In a 500 mL of canonical flask equipped with a reflux condenser, pressure equalized dropping funnel and a nitrogen inlet, there was added 52 mL of distilled water and 0.68 g 2,2'-azobis(2-methyl propiondiamidine dihydrochloride ($2.5 \times 10^{-3}$ mol). While passing a nitrogen flow from the solution, 84.8 g N,N-diallyl morpholinium p-toluenesulfonate (0.25 mol) was added and stirred until clear solution (approximately 45 min) had obtained. The nitrogen flow was stopped and the system was closed. The polymerization was conducted for 8 h under continuous stirring at 65° C. The reaction content was cooled to room temperature and poured into 180 mL acetone. The polymer precipitated was collected by suction, washed with acetone 25 mL and dried at 80° C. for 24 h. The resulting hygroscopic polymer (80.2 g) was stored in tightly closed bottle.

EXAMPLE 11

Polymerization of N,N-Diallyl Morpholinium Oleate:

In a 500 mL of canonical flask equipped with a reflux condenser, pressure equalized dropping funnel and a nitrogen inlet, there was added a mixture of 40 mL methanol and 20 mL distilled water. Then 0.68 g 2,2'-azobis(2-methyl propiondiamidine dihydrochloride ($2.5 \times 10^{-3}$ mol) was dissolved in this solution, while passing a nitrogen flow. To the solution, 104.0 g N,N-diallyl morpholinium oleate (0.25 mol) was added and stirred until clear solution (approximately 60 min) had obtained. The nitrogen flow was stopped and the system was closed. The polymerization was conducted for 8 h under continuous stirring at 65° C. The reaction content was cooled to room temperature and poured into 150 mL acetone. The polymer precipitated was collected by suction, washed with acetone 25 mL and dried at 80° C. for 24 h. The resulting soft polymer (99.8 g) was stored in tightly closed bottle.

EXAMPLE 12

Copolymerization of N,N-Diallyl Morpholinium Bromide with Hydroxyethymethacrylate (HEMA):

In a 500 mL of canonical flask equipped with a reflux condenser, pressure equalized dropping funnel and a nitrogen inlet, there was added 35 mL of distilled water and 0.68 g 2,2'-azobis(2-methyl propiondiamidine) dihydrochloride ($2.5 \times 10^{-3}$ mol). While passing a nitrogen flow from the solution, 31 g N,N-diallyl morpholinium bromide (0.125 mol) and 16.25 g 2-hydroxyethylmethacrylate (HEMA) (0.125 mol) were added and stirred until clear solution (approximately 30 min) had obtained. The nitrogen flow was stopped and the system was closed. The reaction was conducted for 8 h under continuous stirring at 65° C. The reaction content was cooled to room temperature and poured into 100 mL acetone. The polymer precipitated was collected by suction, washed with acetone 25 mL and dried at 80° C. for 24 h. The resulting polymer (46.7 g) was stored in tightly closed bottle.

EXAMPLE 13

Copolymerization of N,N-Diallyl Morpholinium Bromide with N-Vinyl Pyrrolidinone (NVP):

In a 500 mL of canonical flask equipped with a reflux condenser, pressure equalized dropping funnel and a nitrogen inlet, there was added 35 mL of distilled water and 0.68 g 2,2'-azobis(2-methyl propiondiamidine) dihydrochloride ($2.5 \times 10^{-3}$ mol). While passing a nitrogen flow from the solution, 31 g N,N-diallyl morpholinium bromide (0.125 mol) and 13.9 g N-vinyl 2-pyrrolidinone (0.125 mol) were added and stirred until clear solution (approximately 30 min) had obtained. The nitrogen flow was stopped and the system was closed. The reaction was conducted for 8 h under continuous stirring at 65° C. The reaction content was cooled to room temperature and poured into 100 mL acetone. The polymer precipitated was collected by suction, washed with acetone 25 mL and dried at 80° C. for 24 h. The resulting polymer (41.1 g) was stored in tightly closed bottle.

EXAMPLE 14

Copolymerization of N,N-Diallyl Morpholinium Bromide with N-Vinyl Formamide (NVF):

In a 500 mL of canonical flask equipped with a reflux condenser, pressure equalized dropping funnel and a nitrogen inlet, there was added 35 mL of distilled water and 0.68 g 2,2'-azobis(2-methyl propiondiamidine) dihydrochloride ($2.5 \times 10^{-3}$ mol). While passing a nitrogen flow from the solution, 31 g N,N-diallyl morpholinium bromide (0.125 mol) and 8.9 g N-vinyl formamide 0.125 mol) were added and stirred until clear solution (approximately 30 min) had obtained. The nitrogen flow was stopped and the system was closed. The reaction was conducted for 8 h under continuous stirring at 65° C. The reaction content was cooled to room temperature and poured into 120 mL acetone. The polymer precipitated was collected by suction, washed with acetone 25 mL and dried at 80° C. for 24 h. The resulting polymer (37.6 g) was stored in tightly closed bottle.

It is another object of this invention to provide hydrolysis proof antibacterial quaternary ammonium polymers exhibiting broad spectrum of microbiological activity at 0.2-2% concentrations and lower toxicites. The term "antimicrobial," used herein refers to the ability of killing at least some types of microorganisms. The polymers introduced in the present invention have microbicidal activity (antimicrobial) against a broad spectrum of pathogenic microorganisms. Table-1 shows results of some standard antimicrobial tests of polydiallyl morpholinium with bromide counter anion.

TABLE 1

Standard antibacterial effect test of poly (diallyl morpholinium bromide) in aqueous solution against some common bacteria.

| Bacteria | Source | Polym Conc[a] | Cell growth inhibition[b] | Method | Result[c] (Log R) |
|---|---|---|---|---|---|
| Escherichia coli | ATCC 10536 | 1.0% | ++ | EN1040 | >5.1 |
| Pseudomonas aeruginosa | ATCC 15442 | 1.0% | ++ | EN1040 | ~5.0 |
| Staphylococcus aureus | ATCC 6538 | 1.0% | ++ | ASTM E2149-01 | >5.3 |

[a]Polymer: Poly (diallyl morpholinium bromide),
[b]Medium: Mueller-Hinton agar, abbreviation: +, denotes effective, ++ very effective and − means ineffective,
[c]Contact time 10 min at 20° C.

These are some representative examples of antibacterial performances of the polymers and copolymers described in this embodiment. One striking result of the antibacterial effect of poly (diallyl morpholinium) polymer is its efficiency against *Pseudomonas aeruginosa* which is one of the most detrimental bacteria in hospitals. The homopolymer with borate anion described herein was tested against *Escherichia coli* by cell growth inhibition method. The efficiency was found even higher comparison to the polymer with bromide counter anio), impling positive contribution of the borate anion. Antibacterial effects of the polymers and copolymers presented in this embodiment are not confined to the bacteria listed in Table-1 and the table shows only some representative examples.

The invention claimed is:
1. A process for manufacturing N,N-diallyl ammonium polymers and copolymers comprising the steps of:
preparing N-allyl morpholine by reacting morpholine with allyl bromide under continuous and selective water removal;
quaternizing the obtained N-allyl morpholine by reacting with allyl bromide in a dry atmosphere comprising adding 0.1 g solid KI for each half mole of N-allyl morpholine together with 2 mL dry acetone to obtain a solid product easily breakable by a blender;
polymerizing a composition comprising N,N-diallyl morpholinium monomers having bromide or chloride counter anions in 40-60% aqueous solutions using 2,2'-azobis(2-methyl propiondiamidine) dihydrochloride as a radical initiator yielding high molecular weight polymers or copolymers; and
isolating monomer free polymers or copolymers by re-precipitation in a water-acetone mixture;
wherein the process optionally includes exchanging N,N-diallyl morpholinium chloride or bromide counter anions with borate, oleate or p-toluenesulfonate anions partially or completely prior to the polymerizing step or after the polymerizing step.

2. The process according to claim 1, further comprising preparing antibacterial formulations comprising:
N,N-diallyl morpholinium polymers or copolymers; and
a solvent,
wherein the solvent is selected from the group consisting of water, water-dimethylformamide, and water-N methyl pyrrolidone.

3. The process according to claim 1, wherein the composition of the polymerizing step further comprises comonomers selected from the group consisting of N-vinyl formamide (NVF), N-vinyl pyrrolidinone (NVP) and 2-hydroxyethyl methacrylate (HEMA).

4. The process according to claim 3, wherein the comonomers are present in the composition of the polymerizing step in an amount between 5% and 80%.

5. The process according to claim 3, further comprising preparing antibacterial formulations or composites comprising N,N-diallyl morpholinium copolymerized with 20-80% HEMA comonomers.

6. The process of claim 1, further comprising preparing antibacterial rubbery composites comprising diallyl morpholinium polymer having oleate counter anions present in an amount in the range of from 1-20% by weight of the antibacterial rubbery composite.

7. The process according to claim 1, further comprising preparing antibacterial or antimicrobial solutions comprising the diallyl morpholinium polymer or copolymer for supplying bacteria free air or floors.

8. The process according to claim 1, further comprising preparing aqueous formulations comprising the polymers or copolymers of N,N-diallyl morpholinium monomers having special application in killing *Pseudomonas aeruginosa*.

9. The process according to claim 1, further comprising preparing antibacterial formulations comprising the polymers or copolymers of N,N-diallyl morpholinium monomers as a biocide, and additional ingredients selected from the group consisting of surfactants in an amount of from 0.3-5%, diluting organic solvents, skin care additives in an amount of from 1-10%, and combinations thereof.

10. The process of claim 8, wherein the diluting organic solvents are present in an amount of from 5-40%, and wherein the diluting organic solvents are selected from the group consisting of glycerol, pentanol, dodecyl alcohol, and combinations thereof.

\* \* \* \* \*